United States Patent
Proksa et al.

(10) Patent No.: US 9,801,605 B2
(45) Date of Patent: Oct. 31, 2017

(54) DETECTION APPARATUS FOR DETECTING PHOTONS TAKING PILE-UP EVENTS INTO ACCOUNT

(71) Applicant: KONINKLIJKE PHILIPS N.V., Eindhoven (NL)

(72) Inventors: Roland Proksa, Neu Wulmstorf (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 520 days.

(21) Appl. No.: 14/362,458

(22) PCT Filed: Dec. 13, 2012

(86) PCT No.: PCT/IB2012/057266
§ 371 (c)(1),
(2) Date: Jun. 3, 2014

(87) PCT Pub. No.: WO2013/093726
PCT Pub. Date: Jun. 27, 2013

(65) Prior Publication Data
US 2014/0328466 A1 Nov. 6, 2014

Related U.S. Application Data

(60) Provisional application No. 61/578,546, filed on Dec. 21, 2011.

(51) Int. Cl.
*A61B 6/03* (2006.01)
*H01L 27/148* (2006.01)
(Continued)

(52) U.S. Cl.
CPC ............ *A61B 6/585* (2013.01); *A61B 6/5258* (2013.01); *G01R 29/0273* (2013.01);
(Continued)

(58) Field of Classification Search
CPC .. A61B 6/00; A61B 6/02; A61B 6/025; A61B 6/03; A61B 6/032; A61B 6/42;
(Continued)

(56) References Cited

U.S. PATENT DOCUMENTS 6,590,957 B1 7/2003 Warburton et al.
7,208,739 B1 4/2007 Yanoff et al.
(Continued)

FOREIGN PATENT DOCUMENTS

CN 101561507 A 10/2009
EP 0410828 A2 1/1991
(Continued)

OTHER PUBLICATIONS

Llopart, X., et al.; Medipix2: a 64-k Pixel Readout Chip with 55-um Square Elements Working in Single Photon Counting Mode; 2002; IEEE Trans. on Nuclear Science; 49(5)2279-2283.
(Continued)

*Primary Examiner* — Anastasia Midkiff

(57) ABSTRACT

The invention relates to a detection apparatus (12) for detecting photons. The detection apparatus comprises a pile-up determining unit (15) for determining whether detection signal pulses being indicative of detected photons are caused by a pile-up event or by a non-pile-up event, wherein a detection values generating unit (16) generates detection values depending on the detection signal pulses and depending on the determination whether the respective detection signal pulse is caused by a pile-up event or by a non-pile-up event. In particular, the detection values generating unit can be adapted to reject the detection signal pulses caused by pile-up events while generating the detection values. This allows for an improved quality of the generated detection values.

11 Claims, 3 Drawing Sheets

(51) Int. Cl.
- H01L 27/146 (2006.01)
- G06F 7/64 (2006.01)
- G01T 1/18 (2006.01)
- H03K 5/125 (2006.01)
- H03K 21/40 (2006.01)
- G01R 29/02 (2006.01)
- G01R 1/08 (2006.01)
- G01R 29/24 (2006.01)
- A61B 6/00 (2006.01)
- H03K 5/24 (2006.01)
- G01R 29/033 (2006.01)
- H03K 5/1252 (2006.01)
- G01R 29/027 (2006.01)
- G01R 29/08 (2006.01)
- G01T 1/17 (2006.01)

(52) U.S. Cl.
CPC .............. *G01R 29/033* (2013.01); *G01T 1/18* (2013.01); *G06F 7/64* (2013.01); *H01L 27/14856* (2013.01); *H03K 5/1252* (2013.01); *H03K 5/2463* (2013.01); *A61B 6/4241* (2013.01); *A61B 6/5205* (2013.01); *A61B 6/582* (2013.01); *A61B 2560/0223* (2013.01); *A61B 2560/0238* (2013.01); *G01R 29/0878* (2013.01); *G01R 29/24* (2013.01); *G01T 1/171* (2013.01); *H03K 21/40* (2013.01)

(58) Field of Classification Search
CPC ....... A61B 6/4208; A61B 6/4241; A61B 6/48; A61B 6/482; A61B 6/52; A61B 6/5205; A61B 6/5258; A61B 6/58; A61B 6/582; A61B 6/585; A61B 2560/00; A61B 2560/02; A61B 2560/0223; A61B 2560/0238; A61B 2576/00; G06T 7/00; G06T 7/0012; G06T 5/00; H04N 5/30; H04N 5/32; H04N 5/321; H04N 5/325; H02L 27/00; H02L 27/14; H02L 27/142; H02L 27/1446; H02L 27/146; H02L 27/14601; H02L 27/14658; H02L 27/14676; H02L 27/148; H02L 27/14806; H02L 27/14856; H02L 27/14893; H02L 27/30; H02L 27/305; H02L 27/307; H02L 27/308; G06F 7/62; G06F 7/64; G06F 7/68; G11C 19/28; G11C 19/282; G11C 19/285; G01T 1/00; G01T 1/15; G01T 1/18; G01T 1/20; G01T 1/2006; G01T 1/2018; G01T 1/208; G01T 1/24; G01T 1/245–1/247; G01T 1/36; G01T 1/362; G01T 1/365; G01T 1/366; H03K 17/00; H03K 17/0414; H03K 17/0422; H03K 17/08; H03K 19/00; H03K 19/003; H03K 19/0033; H03K 5/125; H03K 5/1252; H03K 5/22; H03K 5/24; H03K 5/2463; H03K 21/00; H03K 21/08; H03K 21/10; H03K 21/40; H03K 2017/0803; G01R 29/00; G01R 29/02; G01R 29/023; G01R 29/0273; G01R 29/033; G01R 29/08; G01R 29/0864; G01R 29/0871; G01R 29/0878; G01R 29/0892; G01R 29/24; G01R 29/26

See application file for complete search history.

(56) References Cited

U.S. PATENT DOCUMENTS

| | | | |
|---|---|---|---|
| 2003/0033097 A1* | 2/2003 | Tanaka | G01T 1/171 702/60 |
| 2004/0036025 A1 | 2/2004 | Wong et al. | |
| 2006/0276706 A1* | 12/2006 | Klein | G01T 1/171 600/407 |
| 2007/0262251 A1 | 11/2007 | Balan | |
| 2008/0260094 A1* | 10/2008 | Carmi | A61B 6/032 378/19 |
| 2009/0039273 A1* | 2/2009 | Tkaczyk | G01T 1/171 250/370.06 |
| 2009/0074281 A1* | 3/2009 | McFarland | A61B 6/032 382/131 |
| 2010/0193700 A1 | 8/2010 | Herrmann et al. | |
| 2011/0017918 A1* | 1/2011 | Baeumer | G01T 1/17 250/370.11 |
| 2011/0155899 A1 | 6/2011 | Dror et al. | |

FOREIGN PATENT DOCUMENTS

| | | |
|---|---|---|
| GB | 2332513 A | 6/1999 |
| JP | 05203754 | 8/1983 |
| JP | H01-118393 | 8/1989 |
| JP | H06-86084 | 12/1994 |
| WO | 2008146230 A2 | 12/2008 |
| WO | 2011002452 A1 | 1/2011 |

OTHER PUBLICATIONS

Roessl, E., et al.; K-edge imaging in x-ray computed tomography using multi-bin photon counting detectors; 2007; Phys. Biol.; 52:4679-4696.

Takahashi, T., et al.; Recent Progress in CdTe and CdZnTe Detectors; 2000; IEEE Trans. on Nuclear Science; 48(4) 950-959.

* cited by examiner

DETECTION APPARATUS FOR DETECTING PHOTONS TAKING PILE-UP EVENTS INTO ACCOUNT

CROSS REFERENCE TO RELATED APPLICATION

This application is a national filing of PCT application Serial No. PCT/IB2012/057266, filed Dec. 13, 2012, published as WO 2013/093726 A1 on Jun. 27, 2013, which claims the benefit of U.S. provisional application Ser. No. 61/578,546 filed Dec. 21, 2011, which is incorporated herein by reference.

FIELD OF THE INVENTION

The invention relates to a detection apparatus, a detection method and a detection computer program for detecting photons. The invention relates further to an imaging apparatus, an imaging method and an imaging computer program for imaging an object.

BACKGROUND OF THE INVENTION

The article "Medipix2: A 64-k pixel readout chip with 55-μm square elements working in single photon counting mode" by X. Llopart et al., IEEE Transactions on Nuclear Science, volume 49, issue 5, pages 2279 to 2283, October 2002 discloses a photon counting detector, which generates detection values depending on detected photons. In particular, a direct conversion material is used for transforming photons into signal pulses, wherein each signal pulse corresponds to a single photon and wherein the signal pulse height of the respective signal pulse is indicative of the energy of the respective photon. The signal pulses are distributed among several energy bins, wherein for each energy bin a detection value is generated, which is indicative of the number of signal pulses assigned to the respective energy bin.

The resulting energy distribution can be corrupted by limitations of the detector, which may lead to a reduction of the quality of the generated detection values.

SUMMARY OF THE INVENTION

It is an object of the present invention to provide a detection apparatus, a detection method and a detection computer program for detecting photons, which allow generating detection values with an improved quality. It is a further object of the present invention to provide an imaging apparatus, which comprises the detection apparatus, and a corresponding imaging method and imaging computer program for imaging the object.

In a first aspect of the present invention a detection apparatus for detecting photons is presented, wherein the detection apparatus comprises:
a detection unit for detecting photons, wherein the detection unit is adapted to generate detection signal pulses being indicative of the detected photons,
a pile-up determining unit for determining whether a detection signal pulse is caused by a pile-up event or by a non-pile-up event,
a detection values generating unit for generating detection values depending on the detection signal pulses and depending on the determination whether the respective detection signal pulse is caused by a pile-up event or by a non-pile-up event.

Since the pile-up determining unit determines whether a detection signal pulse is caused by a pile-up event or by a non-pile-up event and since the detection values generating unit generates detection values depending on the detection signal pulses and depending on the determination whether the respective detection signal pulse is caused by a pile-up event or by a non-pile-up event, the pile-up effect can be considered relatively accurately, while generating the detection values. This allows improving the quality of the generated detection values.

A pile-up event is preferentially defined by a contribution of several photons to a same detection signal pulse.

The detection unit comprises preferentially a direct conversion material like cadmium cerium (CdCe) or cadmium zinc telluride (CZT) for generating detection signal pulses depending on photons meeting the direct conversion material. Alternatively or in addition, the detection unit can comprise a scintillator material and photodiodes, wherein light pulses can be generated by the scintillator material depending on photons meeting the scintillator material and wherein the photodiodes can detect the generated light pulses and generate detection signal pulses depending on the detected light pulses.

It is preferred that the detection signal pulses generating unit is adapted to reject the detection signal pulses caused by pile-up events and to generate the detection values depending on the detection signal pulses which are caused by a non-pile-up event. Since the detection signal pulses generating unit rejects the detection signal pulses caused by pile-up events, the generation of the detection values is based only on detection signal pulses, which are not corrupted by the pile-up effect, thereby further increasing the quality of the generated detection values.

It is further preferred that the detection signal pulses generating unit is adapted to a) determine a non-pile-up number by counting the detection signal pulses, which are caused by a non-pile-up event, b) determine a pile-up number by counting the detection signal pulses, which are caused by a pile-up event, c) correct the non-pile-up number based on the pile-up number, d) generate a detection value depending on the corrected non-pile-up number. Since the uncorrected pile-up number does not consider pile-up photons, the uncorrected pile-up number corresponds to a number of photons, which is smaller than the number of photons which have actually met the detection apparatus. This reduced non-pile-up number can be corrected based on the pile-up number, thereby improving the quality of the non-pile-up number and, thus, of the generated detection value.

The detection values generating unit can be adapted to provide an expected mean number of photons contributing to a pile-up event and to correct the non-pile-up number by multiplying the pile-up number with the expected mean number of photons contributing to a pile-up event, thereby generating a correction product, and by adding the correction product to the non-pile-up number. The expected mean number is preferentially two, wherein it is assumed that a detection signal pulse, which is caused by a pile-up event, corresponds mainly to two photons having met the detection apparatus, i.e. that the pile-up events are mainly first order pile-up events. Thus, the non-pile-up number can, in this case, reliably be corrected with low computational efforts by adding twice the pile-up number to the uncorrected non-pile-up number. However, the expected mean number of photons contributing to a pile-up event can also be another number. This allows correcting the non-pile-up number, also if a pile-up event is not mainly caused by two photons, but, for instance, by a varying number of photon and/or by a larger number of photons. Higher order pile-up events can therefore be considered.

The detection apparatus comprises preferentially several detection pixels, wherein for each detection pixel a pile-up number and a non-pile-up number can be determined. In an embodiment, the detection apparatus is non-energy-resolving such that for each detection pixel a single detection value is generated at a time. However, preferentially the detection apparatus is an energy-resolving detection apparatus, wherein for each detection pixel several detection values, which correspond to different energies, are generated at a time. Thus, the detection values generating unit can be adapted to a) bin the detection signal pulses, which are caused by a non-pile-up event, into several bins depending on a property of the detection signal pulses, b) determine for each bin a non-pile-up number by counting the detection signal pulses of the respective bin, which are caused by a non-pile-up event, thereby generating a non-pile-up distribution, c) determine a pile-up number by counting the detection signal pulses, which are caused by a pile-up event, d) estimate a pile-up distribution such that the integral of the pile-up distribution corresponds to the product of the determined pile-up number with a provided expected mean number of photons contributing to a pile-up event, e) correct the non-pile-up distribution based on the pile-up distribution, f) generate detection values depending on the corrected non-pile-up distribution.

Preferentially, the detection values generating unit is adapted to estimate the pile-up distribution by assuming that the shape of the pile-up distribution is similar to the shape of the non-pile-up distribution, wherein the pile-up distribution is estimated such that an integral of the pile-up distribution having the shape of the non-pile-up distribution corresponds to the product of the determined pile-up number with the expected mean number of photons contributing to a pile-up event. The expected mean number can be, for instance, two. The correction of the non-pile-up distribution is preferentially performed by adding the estimated pile-up distribution. In another embodiment also the detection signals, which are caused by a pile-up event, can be binned, depending on a property of the detection signal pulses, in particular, depending on the detection signal pulse height, in order to determine a pile-up distribution, which may be used for correcting the non-pile-up distribution.

In particular, the detection values generating unit can be adapted to compare the detection signal pulses with detection signal height pulse thresholds defining energy bins, in order to distribute the detection signal pulses among the energy bins, wherein for each energy bin a detection value is determined being indicative of the non-pile-up number of the detection signal pulses assigned to the respective energy bin. The comparison procedures for comparing the detection signal pulses with respective thresholds are preferentially performed by comparators of the detection values generating unit. The non-pile-up numbers define a non-pile-up distribution which may be corrected based on a respective pile-up distribution.

In an embodiment, for determining whether a respective detection signal pulse is caused by a pile-up event or by a non-pile-up event the pile-up determining unit is adapted to provide a pulse height threshold and to compare the detection signal pulse height of the respective detection signal pulse with the pulse height threshold for determining whether the respective detection signal pulse is caused by a pile-up event or by a non-pile-up event. Moreover, the pile-up determining unit can be adapted to a) determine the temporal length of the respective detection signal pulse, b) provide a temporal length threshold, and c) compare the temporal length of the respective detection signal pulse with the temporal length threshold for determining whether the respective detection signal pulse is caused by a pile-up event or by a non-pile-up event. The pile-up determining unit can also be adapted to a) integrate the respective detection signal pulse for generating a respective integrated value, b) compare the integrated value with the detection signal pulse height of the respective detection signal pulse, thereby generating a comparison result, and c) determine whether a respective detection signal pulse is caused by a pile-up event or by a non-pile-up event based on the comparison result. For instance, a ratio of the detection signal pulse height and of the integrated value can be generated as comparison result, wherein it can be determined whether a respective detection signal pulse is caused by a pile-up event or by a non-pile-up event based on the ratio. Moreover, the pile-up determining unit can be adapted to determine whether a respective detection signal pulse is caused by a pile-up event or by a non-pile-up event based on inconsistency of counting results. These different determination types allow determining whether a detection signal pulse is caused by a pile-up event or by a non-pile-up event reliably with relatively low computational efforts.

In a further aspect of the present invention an imaging apparatus for imaging an object is presented, wherein the imaging apparatus comprises:

a photon source for generating photons for traversing the object, a detection apparatus for detecting the photons after having traversed the object and for generating detection values as defined in claim 1.

The photon source is preferentially a polychromatic x-ray source and the detection apparatus is preferentially adapted to detect x-ray photons, after having traversed the object. The imaging apparatus is preferentially a computed tomography system or an x-ray C arm system, which allow rotating the photon source and the detection apparatus around the object along a trajectory arranged on, for example, an imaginary cylinder or an imaginary sphere. The trajectory is, for example, a circular or helical trajectory.

It is preferred that the imaging apparatus further comprises a reconstruction unit for reconstructing an image of the object based on the generated detection values. In particular, the reconstruction unit can be adapted to reconstruct an image of the object based on generated energy-resolved detection values. It can be adapted to perform, for example, a decomposition technique, which decomposes the detection values into different components, which can be indicative of different materials like bone and soft tissue, and/or different physical effects like the photoelectric effect, the Compton effect or a K-edge effect. A corresponding decomposition technique is disclosed, for example, in the article "K-Edge imaging in x-ray computed tomography using multi-bin photon counting detectors" by E. Roessl and R. Proksa, Physics in Medicine and Biology, volume 52, pages 4679 to 4696 (2007), which is herewith incorporated by reference. The reconstruction unit can further be adapted to reconstruct for at least one component a separate image based on component detection values, which have been determined for the respective component by the decomposition technique.

In a further aspect of the present invention a detection method for detecting photons is presented, wherein the detection method comprises:

detecting photons by a detection unit, wherein the detection unit is adapted to generate detection signal pulses being indicative of the detected photons, determining whether a detection signal pulse is caused by a pile-up event or by a non-pile-up event by a pile-up determining unit, generating detection values depending on the detection signal pulses and depending on the determination whether the respective detection signal pulse is caused by a pile-up event or by a non-pile-up event by a detection values generating unit.

In a further aspect of the present invention an imaging method for imaging an object is presented, wherein the imaging method comprises:

generating photons having different energies for traversing the object by a photon source, detecting the photons for generating detection values.

In a further aspect of the present invention a detection computer program for detecting detection data is presented, wherein the detection computer program comprises program code means for causing a detection apparatus to carry out the steps of the detection method, when the detection computer program is run on a computer controlling the detection apparatus.

In a further aspect of the present invention an imaging computer program for imaging an object is presented, wherein the imaging computer program comprises program code means for causing an imaging apparatus to carry out the steps of the imaging method, when the imaging computer program is run on a computer controlling the imaging apparatus.

It shall be understood that the detection apparatus, the imaging apparatus, the detection method, the imaging method, the detection computer program and the imaging computer program have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
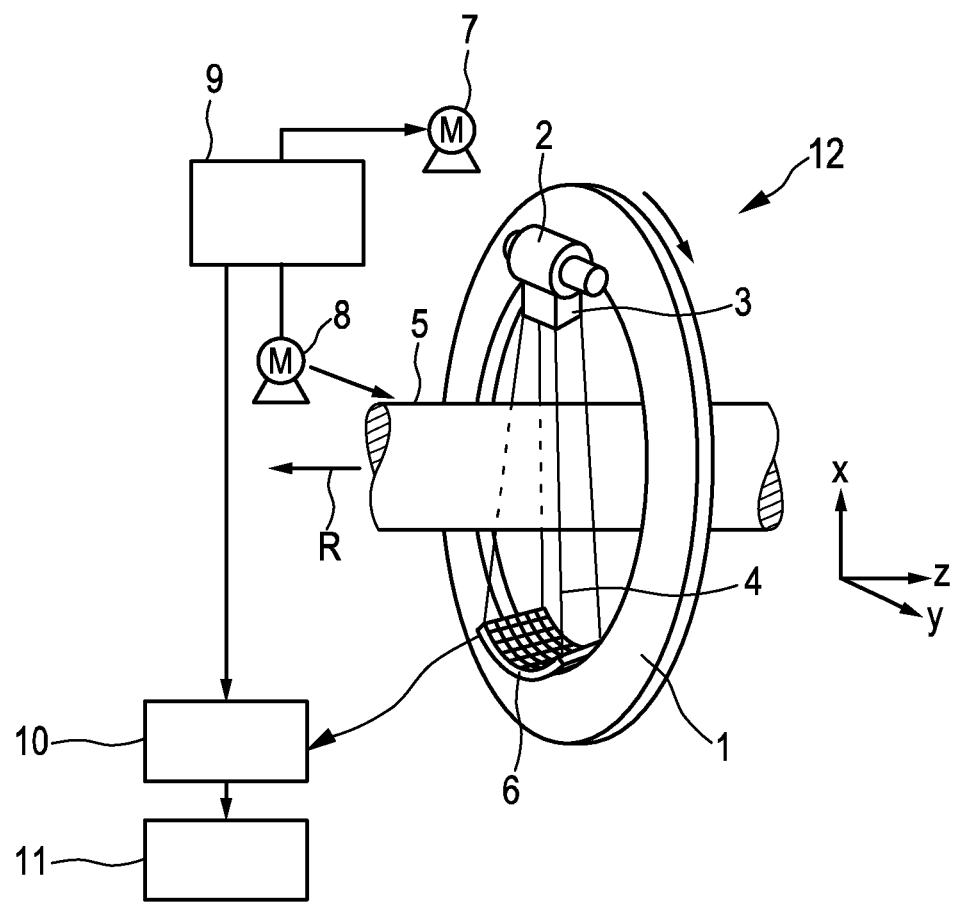
FIG. 1 shows schematically and exemplarily an embodiment of an imaging apparatus for imaging an object.

FIG. 1 shows schematically and exemplarily an imaging apparatus for imaging an object being a computed tomography apparatus 12. The computed tomography apparatus 12 includes a gantry 1, which is capable of rotation about a rotational axis R, which extends parallel to a z direction. A photon source 2, which is, in this embodiment, a polychromatic x-ray tube, is mounted on the gantry 1. The photon source 2 is provided with a collimator 3, which forms, in this embodiment, a conical radiation beam 4 from the photons generated by the photon source 2. The photons traverse an object such as a patient in an examination zone 5, which is, in this embodiment, cylindrical. After having traversed the examination zone 5, the radiation beam 4 is incident on a detection apparatus 6, which comprises a two-dimensional detection surface. The detection apparatus 6 is mounted on the gantry 1.

The computed tomography apparatus 12 comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. These motors 7, 8 are controlled by a control unit 9, for instance, such that the photon source 2 and the examination zone 5 move relative to each other along a helical directory. However, it is also possible that the object is not moved, but that only the photon source 2 is rotated, i.e. that the photon source 2 moves along a circular directory relative to the object or the examination zone 5. Furthermore, in another embodiment, the collimator 3 can be adapted for forming another beam shape, in particular a fan beam, and the detection apparatus 6 can comprise a detection surface, which is shaped corresponding to the other beam shape, in particular to the fan beam.

During a relative movement of the photon source 2 and the examination zone 5, the detection apparatus 6 generates detection values depending on the radiation incident on the detection surface of the detection apparatus 6. The detection values are provided to a reconstruction unit 10 for reconstructing an image of the object based on the detection values. The image reconstructed by the reconstruction unit 10 is provided to a display unit 11 for displaying the reconstructed image.

The control 9 is preferentially also adapted to control the photon source 2, the detection apparatus 6 and the reconstruction unit 10.

Figure 2:
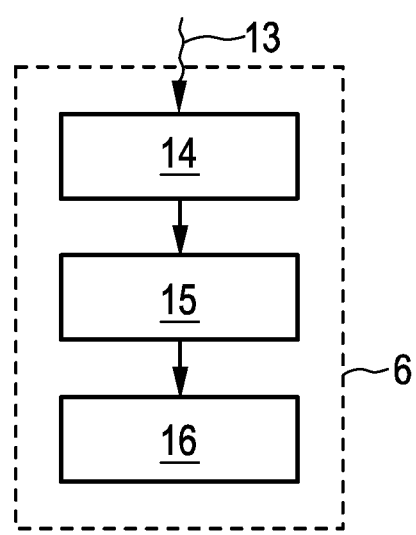
FIG. 2 shows schematically and exemplarily an embodiment of a detection apparatus for detecting photons.

FIG. 2 shows schematically and exemplarily a detection unit 14, a pile-up determining unit 15 and a detection values generating unit 16 of the detection apparatus 6. The detection unit 14 is adapted to detect photons 13 and to generate detection signal pulses having a detection signal pulse height being indicative of the energy of the respective detected photon 13. The pile-up determining unit 15 is adapted to determine whether a detection signal pulse is caused by a pile-up event or by a non-pile-up event, i.e. the pile-up determining unit 15 determines whether a detection signal pulse corresponds to a single photon or to two or more photons. The detection values generating unit 16 is adapted to generate detection values depending on the detection signal pulses and depending on the determination whether the respective detection signal pulse is caused by a pile-up event or by a non-pile-up event.

The detection unit 14 comprises a direct conversion material like CdCe or CZT for generating the detection signal pulses depending on photons meetings the direction conversion material. Preferentially, the detection unit 14 comprises several detection pixels, wherein for each detection pixel a detection signal pulse is generated. Such a detection unit comprising a direct conversion material is disclosed, for example, in the article "Recent progress in CdTe and CdZnTe detectors" by T. Takahashi and S. Watanabe, IEEE Transactions on Nuclear Science, volume 48, issue 4, pages 950 to 959, August 2001, which is herewith incorporated by reference.

In this embodiment, for determining whether a respective detection signal pulse is caused by a pile-up event or by a non-pile-up event the pile-up determining unit 15 is adapted to provide a pulse height threshold and to compare a detection signal pulse height of the respective detection signal pulse with the pulse height threshold for determining whether the respective detection signal pulse is caused by a pile-up event or by a non-pile event. The pulse height threshold is similar to or larger than the maximal expected detection signal pulse height caused by single photons. The pile-up determining unit 15 preferentially comprises comparators for comparing the detection signal pulses with the pulse height threshold.

Alternatively or in addition, the pile-up determining unit can be adapted to determine the temporal length of the respective detection signal pulse, to provide a temporal length threshold, and to compare the temporal length of the respective detection signal pulse with the temporal length threshold for determining whether the respective detection signal pulse is caused by a pile-up event or by a non-pile-up event. Thus, the pile-up determining unit 15 can be adapted to measure the time of each detection signal pulse. Detection signal pulses from single photons have a well-known duration as given, for instance, by a pulse shaper, which may shape the detection signal pulses generated by the detection unit 14, wherein the duration can generally only be exceeded if a detection signal pulse corresponds to several photons. This kind of determining whether the respective detection signal pulse is caused by a pile-up event or by a non-pile-up event can be realized by a comparator of the pile-up determining unit 15, which detects signal levels above a noise floor. If the signal exceeds the noise floor, a timer of the pile-up determining unit 15 can be started. If the timer expires before the signal is again below the noise floor, the respective detection signal pulse can be classified as being caused by a pile-up event.

Furthermore, alternatively or in addition, the pile-up determining unit 15 can be adapted to integrate the respective detection signal pulse for generating a respective integrated value, to compare the integrated value with the detection signal pulse height of the respective detection signal pulse, thereby generating a comparison result, and to determine whether a respective detection signal pulse is caused by a pile-up event or by a non-pile-up event based on the comparison result. The comparison result is preferentially the ratio of the detection signal pulse height to the integrated value of the respective detection signal pulse. Thus, the total charge of a detection signal pulse can be measured by integrating the signal of the detection signal pulse. The resulting integral can be compared to the pulse height using a comparator. Detection signal pulses, which correspond to single photons, will have a well known relation of pulse height to pulse integral. If this relation does not fit to a provided expected range of values, which can be determined, for instance, by calibration measurements, the respective detection signal pulse can be classified as being caused by a pile-up event.

Moreover, also alternatively or in addition, the pile-up determining unit 15 can be adapted to determine whether a respective detection signal pulse is caused by a pile-up event or by a non-pile-up event based on inconsistency of counting results. For example, a lower threshold and a higher threshold can be predefined such that a rising edge of a detection signal pulse, which is not caused by a pile-up event, firstly crosses the lower threshold and then crosses the higher threshold, wherein after having passed the peak of the detection signal pulse a falling edge of the detection signal pulse crosses the higher threshold again in an opposite direction and finally crosses the lower threshold. Moreover, the lower threshold and the higher threshold can be predefined such that a detection signal pulse, which has two maxima with an intermediate minimum caused by two piled-up photons, crosses the higher threshold twice from below the upper threshold to above the upper threshold without an intermediate crossing of the lower threshold. In this case, the pile-up determining unit can be adapted to determine that a respective detection signal pulse is caused by a pile-up event by detecting that the detection signal pulse crosses the higher threshold from below the higher threshold to above the higher threshold twice, without an intermediate crossing of the lower threshold.

The detection signal pulses generating unit 16 is preferentially adapted to reject detection signal pulses caused by pile-up events and to generate the detection values depending on the detection signal pulses which are not caused by a pile-up event. In particular, the detection values generating unit 16 is adapted to bin the detection signal pulses, which are not caused by a pile-up event, into several bins depending on a property of the detection signal pulse. In this embodiment, the binning is performed depending on the detection signal pulse height of the respective detection signal pulse. The detection signal pulse height corresponds to the energy of the photon, to which the respective detection signal pulse corresponds. Thus, by binning the detection signal pulses into several bins depending on the detection signal pulse height the different bins correspond to different energies of the corresponding photons. Preferentially, detection signal pulse height thresholds are provided, wherein each pair of detection signal pulse height thresholds defines a bin, i.e. an energy bin. The detection signal pulses can be distributed among the energy bins by comparing the respective detection signal pulse heights with the detection signal pulse height thresholds. The detection values generating unit 16 comprises preferentially comparators for performing these comparisons with the thresholds.

The detection values generating unit 16 is preferentially further adapted to count for each energy bin a non-pile-up number by counting the detection signal pulses of the respective energy bin, which are caused by a non-pile-up event, thereby generating a non-pile-up distribution. The detection values are then generated depending on the non-pile-up distribution. In particular, for each energy bin a detection value is generated such that the detection values are energy dependent. For instance, a detection value generated for an energy bin can be or can be proportional to the non-pile-up number of the respective energy bin.

In a further embodiment, the detection values generating unit 16 can be adapted to determine a pile-up number by counting all detection signal pulses, which are caused by a pile-up event, and to estimate a pile-up distribution such that the integral of the pile-up distribution corresponds to the product of the determined pile-up number with a provided expected mean number of photons contributing to a pile-up event. The expected mean number of photons is, for instance, two. For estimating the pile-up distribution it can be assumed that the shapes of the non-pile-up distribution and the pile-up distribution are similar such that the pile-up distribution is determined as comprising the shape of the non-pile-up distribution, wherein the integral of the pile-up distribution should be similar to the product of the determined pile-up number with the expected mean number. In an embodiment, the detection values generating unit 16 is adapted to determine the pile-up distribution $D_i$ in accordance with following equation:

$$D_i = mN_p \frac{\tilde{C}_i}{\sum_{k=1}^{N} \tilde{C}_k}, \qquad (1)$$

wherein $\tilde{C}_i$ denotes the uncorrected detection value of the i-th energy bin of the non-pile-up distribution, m denotes the expected mean number of photons contributing to a pile-up event being preferentially two, $N_p$ denotes the pile-up number, and N denotes the number of energy bins.

The detection values generating unit 16 can further be adapted to correct the non-pile-up distribution based on the pile-up distribution, wherein the detection values can be or can be generated depending on the corrected non-pile-up distribution. In particular, the uncorrected non-pile-up distribution $\tilde{C}_i$ can be corrected in accordance with following equation:

$$C_i = \tilde{C}_i + D_i, \qquad (2)$$

wherein $C_i$ denotes the corrected detection value of the i-th energy bin of the corrected non-pile-up distribution.

If in another embodiment the detection apparatus is not energy resolving, i.e. if the detection signal pulse height is not used for performing energy discrimination, the detection values generating unit 16 can be adapted to provide an expected mean number of photons contributing to a pile-up event and to correct the non-pile-up number by multiplying the pile-up number with the expected mean number of photons contributing to a pile-up event, thereby generating a correction product, and by adding the correction product to the non-pile-up number. The expected mean number of photons can be two or a higher number, if a higher order pile-up effect has to be considered.

The reconstruction unit 10 is preferentially adapted to decompose the detection values into different component detection values, which correspond to different components of the object. These different components are, for example, related to different physical effects like the Compton effect, the photoelectric effect and a K-edge effect, and/or the different components can be related to different materials like bone, soft tissue, et cetera of a human being. For instance, the reconstruction unit can use the decomposition technique disclosed in the article "K-Edge imaging in x-ray computed tomography using multi-bin photon counting detectors" by E. Roessl and R. Proksa, Physics in Medicine and Biology, Volume 52, pages 4679 to 4696 (2007), which is herewith incorporated by reference. In an embodiment, the decomposition is performed in accordance with following equation, which is based on the inversion of a physical model describing the measurement process:

$$C_i = \int B_i(E) F(E) e^{-\sum_j^{M_j} A_j P_j(E)} dE, \qquad (3)$$

wherein $C_i$ denotes the detection value of the i-th energy bin, $B_i(E)$ denotes the spectral sensitivity of the i-th energy bin, F(E) denotes the spectrum of the photon source, j is an index for the $M_j$ different components, $A_j$ denotes a line integral of absorption values through the j-th component and $P_j(E)$ denotes the spectral absorption of the j-th component.

If the number of energy bins is at least equal to the number of components, the system of equations can be solved with known numerical methods, wherein the quantities $B_i(E)$, F(E) and $P_j(E)$ are known and the results of solving the system of equations are the line integrals $A_j$. The spectrum of radiation F(E) and the spectral sensitivity $B_i(E)$ are characteristics of the imaging apparatus and the nature of the readout and are known from, for example, corresponding measurements. The spectral absorption $P_j(E)$ of the components, for example, the spectral absorption of bone and soft tissue, is also known from measurements and/or from literature.

The decomposed detection values are, in this embodiment, decomposed projection data, i.e. the line integrals $A_j$, which can each be used for reconstructing a computed tomography image of the object such that, for instance, for each component a component image of the object can be reconstructed. For instance, a Compton component image, a photoelectric component image and/or a K-edge component image can be reconstructed. For reconstructing an image based on the projection data known reconstruction techniques can be used like filtered back projection, Radon inversion, et cetera.

Figure 3:
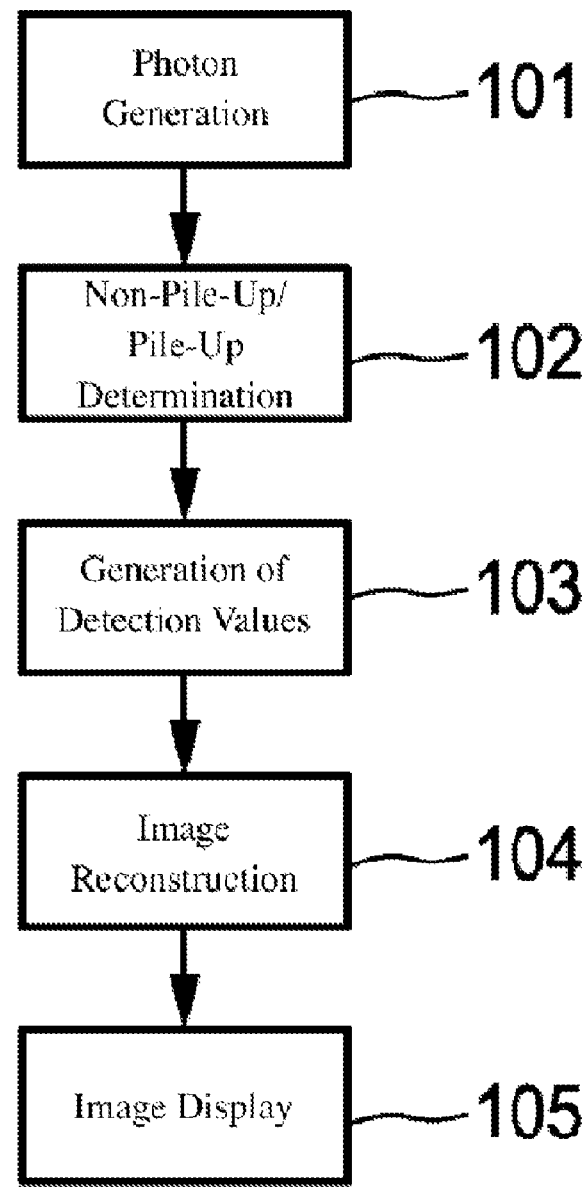
FIG. 3 shows a flowchart exemplarily illustrating an embodiment of an imaging method for imaging an object.

In the following an embodiment of an imaging method for imaging an object will exemplarily be described with reference to a flowchart shown in FIG. 3.

In step 101, the photon source 2 generates photons having different energies, while the photon source 2 and the object are moved relatively to each other, in order to allow the photons to traverse the object in different directions. In particular, the photon source 2 is moved along a circular or helical trajectory around the object, while the detection unit 14 detects the photons, which have traversed the object, and generates detection signal pulses.

In step 102, the pile-up determining unit 14 determines whether a detection signal pulse is caused by a pile-up event or by a non-pile-up event, and, in step 103, the detection values generating unit 16 generates the detection values depending on the detection signal pulses and depending on the determination whether the respective detection signal pulse is caused by a pile-up event or by a non-pile-up event. In particular, for each position of the photon source, for each pixel of the two-dimensional detection surface of the detection unit 14 and for each energy bin a detection value is generated. In step 104, the reconstruction unit 10 reconstructs an image of the object based on the generated detection values by using, for example, a decomposition technique for decomposing the detection values into decomposed detection values, wherein the decomposed detection values are used for reconstructing an image of the object based on computed tomography reconstruction algorithms like a filtered back projection algorithm. In step 105, the reconstructed image is shown on the display unit 11.

Steps 101 to 103 can be regarded as being the steps of a detection method for detecting photons.

Generally, a photon counting detector can suffer from the pile-up effect, which can be present, if a relatively high flux of photons is used as required for medical imaging. Each incoming photon in such a detector generates an electronic pulse of a certain length in time. If two or more photons enter the detector with only a small time difference, the individual pulses overlap such that the detector is unable to separate them, i.e. a single detection signal pulse is generated which is formed by the pulses overlap. Such a pile-up event has two consequences. Firstly, the detector counts only one photon instead of two or more photons. Secondly, if the detector performs energy discrimination by a pulse height analysis, the measured energy will be related to the pulse height of the sum of the pulses and does not adequately represent the energy of one of the photons. The detection apparatus described above with reference to FIG. 2 is able to detect and optionally reject pile-up events from the measurements, in order to not suffer from the degradation of the measurements. The detection apparatus can also be adapted to count pile-up events in the photon counting detector, wherein the counted pile-up events can be used for correction purposes.

Conventional photon counting electronics performs, for example, some analog pulse forming, followed by a discretization stage where the pulse height is discretized with one or more comparators for distributing the pulses among energy bins, wherein the pulses assigned to the energy bins are counted. Regarding the detection apparatus described above with reference to FIG. 2, the detection unit 14 can comprise a direct conversion material for generating current pulses depending on incoming x-ray photons and some analog pulse forming for forming the detection signal pulses based on the current pulses detected. The detection values generating unit can comprise the comparators for discretizing the pulse height and for distributing the detection signal pulses among the energy bins, wherein the detection values generating unit is further adapted to count the detection signal pulses assigned to an energy bin for generating the detection values. In addition, the detection apparatus comprises the pile-up determining unit for analyzing each incoming pulse and for classifying each pulse as pile-up event or normal event, i.e. non-pile-up event. Moreover, the detection values generating unit can be adapted to reject the pulses, i.e. the detection signal pulses, which have been classified as pile-up event, such that the detection values generating unit counts only pulses, which are not caused by a pile-up event. Optionally, the detection values generating unit is further adapted to count the number of classified pile-up events, i.e. count the detection signal pulses caused by a pile-up event, which are optionally binned by the pulse height or charge integral of the event.

The optional function of the detection values generating unit of rejecting detection signal pulses, which are caused by a pile-up event, can be regarded as an addition to pulse counting electronics, in order to ensure that detection signal pulses classified as being caused by a pile-up event are not counted. However, in another embodiment the detection values generating unit is adapted to count detection signal pulses classified as being caused by a pile-up event, in order to provide additional information which can be used to correct for pile-up in a data correction step. The number of pile-up events, i.e. the number of detection signal pulses, in particular, multiplied by two, is a good estimation of the number of missing counts, if detection signal pulses, which are caused by a pile-up event, are rejected. For systems without energy discrimination this quantity can simply be added to the number of non-pile-up counts to get a good pile-up correction.

For systems with energy discrimination, a statistical correction can be performed based on the pile-up counts, because the corresponding numbers are an estimate of additional photons with unknown energy. Advanced pile-up measurement can be done, if the pulse integral of the pile-up events is binned and counted similar to the pulse height analysis. These data can be used for advanced statistical correction, because a sum of the overlapping pulses that causes pile-up is known.

The detection apparatus described above with reference to FIG. 2 can have two advantages in comparison to conventional detection apparatuses. Firstly, the randomness of first order pile-up does not influence the pile-up correction in the proposed system. Secondly, the spectral distribution of the counts within the energy bins is not disturbed. If photons, i.e. detection signal pulses, with pile-up are not counted, the pile-up effect will not disturb the distribution of counts in the energy bins, because they are pile-up free.

Although the detection apparatus has been described as comprising certain units for providing the functions like determining whether a detection signal pulse is caused by a pile-up event or by a non-pile-up event or like generating detection values depending on the detection signal pulses and depending on the determination whether the respective detection signal pulse is caused by a pile-up event or by a non-pile-up event, the detection apparatus can also comprise other digital and/or analog units for realizing the above described functions.

In view of the foregoing, applicant requests withdrawal of the objection.

Although in the above described embodiments the detection apparatus generates energy-resolved detection values, in another embodiment the detection apparatus can also be adapted to generate non-energy-resolved detection values. For instance, the detection signal pulses can be counted without a preceding binning procedure.

Although in the above described embodiments the detection apparatus has been described as being adapted for being used in a computed tomography apparatus, in other embodiments the detection apparatus can also be adapted for being used in another imaging apparatus like nuclear imaging apparatus, for instance, single photon emission computed tomography or positron emission tomography systems imaging apparatus, or X-ray C-arm imaging apparatus.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like the determination whether a detection signal pulse is caused by a pile-up event or by a non-pile-up event, the counting of detection signal pulses, the correction of non-pile-up numbers, in particular, the correction of non-pile-up number distributions, et cetera performed by one or several units or devices can be performed by any other number of units or devices. These operations and/or the control of the imaging apparatus in accordance with the imaging method and/or the control of the detection apparatus in accordance with the detection method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a detection apparatus for detecting photons. The detection apparatus comprises a pile-up determining unit for determining whether detection signal pulses being indicative of detected photons are caused by a pile-up event or by a non-pile-up event, wherein a detection values generating unit generates detection values depending on the detection signal pulses and depending on the determination whether the respective detection signal pulse is caused by a pile-up event or by a non-pile-up event. In particular, the detection values generating unit can be adapted to reject the detection signal pulses caused by pile-up events while generating the detection values. This allows for an improved quality of the generated detection values.

The invention claimed is:

1. A detection apparatus for detecting photons, the detection apparatus comprising:
   a detection unit for detecting photons, wherein the detection unit is adapted to generate detection signal pulses being indicative of the detected photons,
   a pile-up determining unit for determining whether a detection signal pulse is caused by a pile-up event or by a non-pile-up event,
   a detection values generating unit for generating detection values depending on the detection signal pulses and depending on the determination whether the respective detection signal pulse is caused by a pile-up event or by a non-pile-up event
   wherein the detection values generating unit is adapted to:
   bin the detection signal pulses, which are caused by a non-pile-up event, into several bins depending on a property of the detection signal pulses,
   determine for each bin a non-pile-up number by counting the detection signal pulses of the respective bin, which are caused by a non-pile-up event, thereby generating a non-pile-up distribution,
   determine a pile-up number by counting the detection signal pulses, which are caused by a pile-up event,
   estimate a pile-up distribution by assuming a shape of the pile-up distribution is similar to a shape of the non-pile-up distribution such that the integral of the pile-up distribution corresponds to the product of the determined pile-up number with a provided expected mean number of photons contributing to a pile-up event,
   correct the non-pile-up distribution based on the pile-up distribution,
   generate detection values depending on the corrected non-pile-up distribution.

2. The detection apparatus as defined in claim 1, wherein the expected mean number is two.

3. The detection apparatus as defined in claim 1, wherein each detection signal pulse has a detection signal pulse height, wherein for determining whether a respective detection signal pulse is caused by a pile-up event or by a non-pile-up event the pile-up determining unit is adapted to provide a pulse height threshold and to compare a detection signal pulse height of the respective detection signal pulse with the pulse height threshold for determining whether the respective detection signal pulse is caused by a pile-up event or by a non-pile-up event.

4. The detection apparatus as defined in claim 1, wherein for determining whether a respective detection signal pulse is caused by a pile-up event or by a non-pile-up event the pile-up determining unit is adapted to:
   determine the temporal length of the respective detection signal pulse,
   provide a temporal length threshold,
   compare the temporal length of the respective detection signal pulse with the temporal length threshold for determining whether the respective detection signal pulse is caused by a pile-up event or by a non-pile-up event.

5. The detection apparatus as defined in claim 1, wherein each detection signal pulse has a detection signal pulse height, wherein for determining whether a respective detection signal pulse is caused by a pile-up event or by a non-pile-up event the pile-up determining unit is adapted to:
   integrate the respective detection signal pulse for generating a respective integrated value,
   compare the integrated value with the detection signal pulse height of the respective detection signal pulse, thereby generating a comparison result,
   determine whether a respective detection signal pulse is caused by a pile-up event or by a non-pile-up event based on the comparison result.

6. An imaging apparatus for imaging an object, the imaging apparatus comprising:
   a photon source for generating photons for traversing the object,
   a detection apparatus for detecting the photons after having traversed the object and for generating detection values as defined in claim 1.

7. The imaging apparatus as defined in claim 6, wherein the imaging apparatus further comprises a reconstruction unit for reconstructing an image of the object based on the generated detection values.

8. A detection method for detecting photons, the detection method comprising:
   detecting photons by a detection unit, wherein the detection unit is adapted to generate detection signal pulses being indicative of the detected photons,
   determining whether a detection signal pulse is caused by a pile-up event or by a non-pile-up event by a pile-up determining unit,
   generating detection values depending on the detection signal pulses and depending on the determination whether the respective detection signal pulse is caused by a pile-up event or by a non-pile-up event by a detection values generating unit, wherein the detection values generating unit:
   bins the detection signal pulses, which are caused by a non-pile-up event, into several bins depending on a property of the detection signal pulses,
   determines for each bin a non-pile-up number by counting the detection signal pulses of the respective bin, which are caused by a non-pile-up event, thereby generating a non-pile-up distribution,
   determines a pile-up number by counting the detection signal pulses, which are caused by a pile-up event,
   estimates a pile-up distribution by assuming a shape of the pile-up distribution is similar to a shape of the non-pile-up distribution such that the integral of the pile-up distribution corresponds to the product of the determined pile-up number with a provided expected mean number of photons contributing to a pile-up event,
   corrects the non-pile-up distribution based on the pile-up distribution, and
   generates detection values depending on the corrected non-pile-up distribution.

9. An imaging method for imaging an object, the imaging method comprising:
   generating photons having different energies for traversing the object by a photon source,
   detecting the photons for generating detection values as defined in claim 8.

10. A detection computer program for detecting detection data, the detection computer program comprising program code means for causing a detection apparatus to carry out the steps of the detection method as defined in claim 8, when the detection computer program is run on a computer controlling the detection apparatus.

11. An imaging computer program for imaging an object, the imaging computer program comprising program code means for causing an imaging apparatus to carry out the steps of the imaging method as defined in claim 9, when the imaging computer program is run on a computer controlling the imaging apparatus.

\* \* \* \* \*